Figure 1:
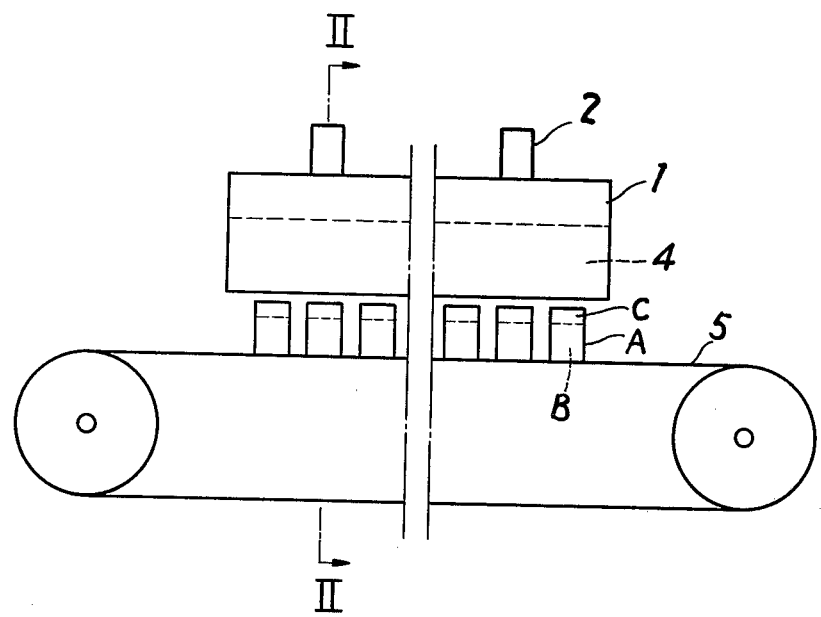

United States Patent [19]
Daigo et al.

[11] 3,956,476
[45] May 11, 1976

[54] BARIUM SULFATE CONTRAST MEDIUM CONTAINING ASCORBIC ACID, ERYTHORBIC ACID OR A WATER-SOLUBLE SALT THEREOF

[75] Inventors: Koji Daigo; Shinichi Okuyama, both of Sakai; Kyuzo Oda, Suita, all of Japan

[73] Assignee: Sakai Chemical Industry Company Ltd., Japan

[22] Filed: June 12, 1973

[21] Appl. No.: 369,312

[30] Foreign Application Priority Data
Sept. 14, 1972 Japan............................ 47-92562

[52] U.S. Cl................................. 424/4; 424/164; 424/359; 424/366; 424/361; 424/362; 424/363
[51] Int. Cl.² ........................................ A61K 29/02
[58] Field of Search ........................................ 424/4

[56] References Cited
UNITED STATES PATENTS

| | | |
|---|---|---|
| 2,680,089 | 6/1954 | Lowy ........................... 424/4 |
| 2,746,906 | 5/1956 | Novak et al. ................... 424/4 |
| 3,235,462 | 2/1966 | Wolfson ......................... 424/4 |
| 3,236,735 | 2/1966 | Brown ........................... 424/4 |
| 3,539,682 | 11/1970 | Eriksson ........................ 424/4 |
| 3,689,630 | 9/1972 | Kikuchi et al. ................. 424/4 |

FOREIGN PATENTS OR APPLICATIONS 481,652   1/1970   Switzerland............................ 424/4

Primary Examiner—Stanley J. Friedman
Assistant Examiner—Vera C. Clarke
Attorney, Agent, or Firm—Larson, Taylor and Hinds

[57] ABSTRACT

An aqueous barium sulfate contrast medium which comprises barium sulfate, carbon dioxide, a suspending agent and an additive selected from the group consisting of ascorbic acid, erythorbic acid and a water-soluble salt thereof, the barium sulfate concentration being at least 750 grams per liter of the medium, the carbon dioxide concentration being 0.2 to 4 gas volumes and the additive concentration being in the range of 1 mg% to 150 mg% is disclosed.

3 Claims, 2 Drawing Figures

BARIUM SULFATE CONTRAST MEDIUM CONTAINING ASCORBIC ACID, ERYTHORBIC ACID OR A WATER-SOLUBLE SALT THEREOF

This invention relates to a barium sulfate contrast medium used in the X-ray photography or fluoroscopicity of the digestive system, and more particularly to an aqueous suspension barium sulfate contrast medium having a high concentration but a low viscosity and to a process for manufacturing a canned barium sulfate contrast medium.

In recent years a double contrast method has been developed and adopted widely in examining the digestive system with a barium sulfate contrast medium. In this method the barium sulfate is first administrated and then a gas such as air is introduced so as to form a double image of positive contrast medium of barium sulfate and a negative medium of gas. According to the above method not only the marginal area but also the central portion of the image can be well detected, hence close examination will be possible.

A barium sulfate contrast medium suitable for this method must have a high barium sulfate concentration, low viscosity for easy administration, excellent dispersibility and a property to permit barium sulfate to adhere to every minute part of the digestive system and mucous membrane. In order to obtain a barium sulfate contrast medium fulfilling the above requirements the present inventors have continued to study and found that when carbon dioxide is contained in a barium sulfate suspension in combination with a suspending agent the contrast medium having the above properties can be obtained.

However, the viscosity of the medium is occasionally liable to increase due to the physical characteristics of barium sulfate per se and the carbon dioxide contained therein, making the medium difficult to administer orally. When the above contrast medium is to be canned, moreover, various problems are encountered. In a canned food it has been essential to reduce the volume of head space of the can as far as possible, since the air remaining in the can gives rise to corrosion. Usually the head space in the conventional canned food is, therefore, strictly regulated to less than about 1 volume %, based on the volume of the can. However, it is difficult to apply the above techniques to the preparation of canned barium sulfate contrast medium for the following reasons. Barium sulfate contrast medium is usually aministrated without cooling unlike beer or like aerated drinks so as to avoid an adverse effect on the stomach and other digestive organs. With the canned contrast medium containing carbon dioxide, therefore, the gas is liable to blow out when the can is opened, if the head space of the can is as small as in the conventional canned products. Further, it is usually preferable to open the canned contrast medium for administration after agitation to make the medium homogeneous, but such agitation is difficult and will accelerate the blowing out of the medium if it is canned with a small head space.

To avoid such problems it is necessary to increase the head space of the can to at least 3 volume %, based on the volume of the can. However, if the head space is enlarged to such extent, the resulting can will be corroded in a relatively short period of time due to the presence of air therein. Such corrosion can not be prevented by the conventional methods, for example, by deaeration and/or by replacement with nitrogen gas.

An object of the invention is to provide a barium sulfate contrast medium suitable for the double contrast method, which has a high order of barium sulfate concentration but a low viscosity for easy oral administration.

Another object of the invention is to provide a method for producing a canned preparation of barium sulfate contrast medium having an enlarged head space free from the corrosion of the can.

These and other objects and advantages of the invention will be apparent from the following description.

The aqueous barium sulfate contrast medium of the present invention, which is suitable for double contrast method and has a high barium sulfate concentration but a low viscosity, comprises barium sulfate, carbon dioxide, a suspending agent and an additive selected from the group consisting of ascorbic acid, erythorbic acid and a water-soluble salt thereof, the barium sulfate concentration being at least 750 grams per liter of the medium, the carbon dioxide concentration being 0.2 to 4 gas volumes and the additive concentration being in the range of 1 mg % to 150 mg %. The term "gas volume" means the volume of the gas dissolved in one volume of the suspension at 60°F and at 760 mmHg.

According to the research of the present inventors it has been found that when ascorbic acid, erythorbic acid or a water-soluble salt thereof is added to a barium sulfate contrast medium having a high barium sulfate concentration and containing carbon dioxide and a suspending agent, the viscosity of the contrast medium is markedly reduced free from any adverse effect thereon, hence easy to administer orally.

Thus the contrast medium of the invention has a high concentration but low viscosity and is stable and suitable for oral administration and the double contrast method. When the medium is administrated, the carbon dioxide contained in the medium will expand within the digestive canal to press barium sulfate against the inner wall of the canal, thereby forming a smooth, continuous and uniform coating on the surface of the canal without allowing the formation of lumps. The presence of carbon dioxide makes it possible to photograph the digestive system by the double contrast method without introduction of a gas after administration of the contrast medium and gives a palatable and refreshing taste like that of aerated water.

In the invention barium sulfate of finer grain is preferred, and generally barium sulfate of an average particle size of 0.02 to 2 $\mu$ may be used, the most preferable being those having an average particle size of smaller than 1 $\mu$. The barium sulfate is contained in the present suspension in a high concentration of at least 750 grams, usually 750 to 1500 grams, and preferably 750 to 1200 grams, per liter of the suspension.

The suspension of the invention should contain carbon dioxide, in the range of 0.2 to 4 gas volumes. If the carbon dioxide is used in excess of the above amount, a special pressure vessel will become necessary and when the vessel is opened for administration, the suspension will blow out, whereas if a less amount of the gas is used, the stability of the suspension can not be improved sufficiently. A desirable amount of carbon dioxide is in the range of 0.4 – 2.0 gas volumes.

The conventional suspending agents, such as sodium carboxymethyl cellulose, sodium alginate, gelatin, tragacanth, acacia, etc. can be used for the purpose. The amount of the suspending agent used can be suitably selected according to the kinds of the agent used, the barium sulfate concentration of the suspension, etc., but generally it may be in the range of 0.2 – 10 weight percent. A preferable amount of sodium carboxymethyl cellulose and sodium alginate is 0.4 to 2.0 weight percent and that of gelatin, tragacanth and acacia is 1 to 10 weight percent, based on the weight of the barium sulfate.

In the present invention it is essential to add ascorbic acid, erythorbic acid or water-soluble salts thereof to the contrast medium, whereby the viscosity is markedly reduced to assure easy oral administration without adversely affecting the properties of the contrast medium. Preferable examples of the water-soluble salts are sodium ascorbate, potassium ascorbate, sodium erythorbate, potassium erythorbate and like alkali metal salts. The additives, i.e., ascorbic acid, erythorbic acid and water-soluble salts thereof, can be used singly or in admixture with one another. The additives can display reduction effect on the viscosity of the contrast medium even when used in such a small amount as 1 mg%, and the effect markedly increases in an amount of not less than 3 mg%. Larger amounts can be added with an increased reduction effect on the viscosity free from adverse results, but the use of more than 150 mg% will result in no improved effect. Therefore, it is preferable to use such additives in an amount of 3 to 50 mg%, most preferable being in the range of 5 to 30 mg%. The reduction effect on viscosity with the above specific additives can be seen in Table 1 below, which shows the viscosities of a sample contrast media prepared in accordance with the method disclosed in Example 1, using predetermined amounts of the additives, to produce the contrast media comprising 100 w/v% of barium sulfate, 1.0 w/v% of sodium carboxymethyl cellulose and 1 vol. of carbon dioxide, the viscosity being determined at 25°C by using a Brookfield viscometer.

Table 1

| Amount of additives(mg%) | (Viscosity in cps) Additives used | | | |
|---|---|---|---|---|
| | Ascorbic acid | Sodium ascorbate | Erythorbic acid | Sodium erythorbate |
| 0 | 886 | 886 | 886 | 886 |
| 1 | 534 | 549 | 544 | 577 |
| 3 | 348 | 348 | 341 | 367 |
| 5 | 292 | 332 | 307 | 350 |
| 10 | 265 | 309 | 291 | 305 |
| 20 | 235 | 209 | 264 | 287 |
| 50 | 230 | 280 | 258 | 307 |
| 100 | 235 | 295 | 243 | 310 |
| 150 | 238 | 300 | 250 | 315 |

According to the method for preparing a canned preparation of the contrast medium of this invention, the contrast medium is placed in a can and the air present in the head space thereof is replaced with carbon dioxide gas flowing in a downward direction continuously, followed by sealing. In this method it is critical to use carbon dioxide gas as a replacing gas and to make the gas flow downward continuously, whereby the air in the head space is effectively replaced with carbon dioxide gas, though a slight amount of air may still remain in the head space. The oxygen in the remaining air is chemically consumed during storage by the action of ascorbic acid, erythorbic acid or a salt thereof contained in the present contrast medium of the invention. Therefore, the head space of the can can be enlarged, free from undesired corrosion of the can, to not less than 3 volume %, based on the volume of the can, which is 3 or more times larger than that of the conventional canned products. According to the above method it is possible to increase the head space of the can to 20 volume %, based on the volume of the can. Preferable head space is in the range of 8 to 20 volume %, based on the volume of the can.

In the above method for preparing a canned contrast medium it is critical to use carbon dioxide gas as a replacing gas and to make the gas flow downward continuously. If an inert gas other than carbon dioxide, such as nitrogen, is used as a replacing gas, it can not be effectively substituted for the air in the head space, making it difficult to increase the volume of the head space. Even if carbon dioxide is used as a replacing gas, effective substitution of carbon dioxide for the air in the head space can not be attained unless carbon dioxide is allowed to flow downward continuously.

Figure 2:
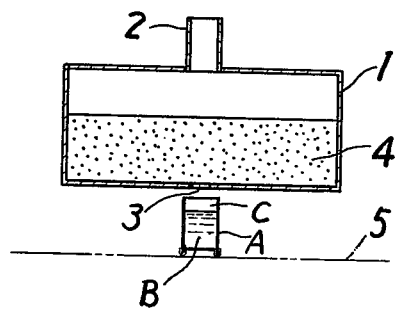

For a better understanding of the invention, a method for producing canned preparation of the present contrast medium is disclosed below in reference to the attached drawings, in which:

FIG. 1 is a side diagram showing one example of the apparatuses used in the present method, and FIG. 2 is a view in section taken along the line II—II in FIG. 1.

Referring now to the drawings, a duct 1 is provided on the upper surface with pipes 2 for supplying carbon dioxide gas thereto and at the center of the bottom thereof with a slit 3, opened longitudinally, for discharging carbon dioxide gas therefrom. In the duct 1 is placed an air-permeable material 4, such as polymer foams having open pores, nonwoven fabrics, etc., so as to discharge the gas uniformly from the duct 1 through the slit 3. Below the duct 1 there is placed a conveyer 5 for carrying cans A containing barium sulfate contrast medium B. Head space of the can A is designated at C.

Carbon dioxide gas supplied from the pipes 2 to the duct 1 is discharged uniformly from the slit 3 through the air-permeable material 4. The gas discharged flows downward continuously at a constant rate and is substituted for the air in the head space C of the can A. By this method the substitution can be conducted very effectively and almost all air in the head space C is replaced with the carbon dioxide gas.

In accordance with the above method it is preferable to control the linear velocity of carbon dioxide gas discharged from the slit 3 and flowing downward continuously within the range of 500 to 5,000 cm/min, most preferably within the range of 1,000 to 3,000 cm/min. As far as the gas is allowed to flow downward continuously and the linear velocity thereof is controlled to the above range, any apparatus other than that shown in the drawings can be used in the invention. In the apparatus illustrated the width of the slit 3 is not critical and can vary freely depending on the predetermined volume of the head space and the diameter of the can. Usually a narrow slit is preferable, though the width thereof may be larger than a diameter of the can to be used. For example, with a can, 350 ml in volume and 65 mm in diameter, the slit is preferably 0.5 to 10.0 mm in width. The length of the slit can also vary over a wide range depending on the feeding velocity of the can and is not critical.

In accordance with the method for preparing canned contrast medium, the additive, i.e., ascorbic acid, erythorbic acid or a water-soluble salt thereof can be added to the contrast medium before or after substitution of carbon dioxide gas for the air in the head space. Preferably, it is added thereto before the gas substitution. Subsequently, the can is sealed in the conventional manner to produce a canned preparation of barium sulfate contrast medium.

For a better understanding of the invention examples are given below.

EXAMPLE 1

In 82 liters of water were dissolved 3 kg of sodium carboxymethyl cellulose, and in the solution were suspended 300 kg of barium sulfate. After the suspension was cooled to 5° to 10°C, 450 g of ascorbic acid were dissolved therein. In a resin coated steel can, 350 ml in volume, were placed 150 ml of the resultant suspension and 150 ml of aerated water containing 2.0 gas volumes of carbon dioxide to produce barium sulfate contrast medium.

The air in the head space of the can was replaced with carbon dioxide gas flowing downward at a linear velocity of 1000 cm/min. and the can was immediately sealed.

The changes in the amount of remaining air in the can with the lapse of time are shown in Table 2 below, which also shows test results for a canned product prepared in the same manner as above without using ascorbic acid for comparative purposes.

Table 2

| Lapse of time | Ascorbic acid added (mg%) | Remaining air (ml) | Remaining oxygen (ml) |
|---|---|---|---|
| 0 | 0 | 16.0 | 1.2 |
|  | 150 | 6.3 | 1.1 |
| 1 week | 0 | 6.0 | 1.2 |
|  | 150 | 5.8 | 0.5 |
| 3 weeks | 0 | 5.9 | 1.1 |
|  | 150 | 5.3 | 0 |

From the above test results it is seen that oxygen in the can is reduced with the lapse of time and finally reaches zero after three weeks of storage, when the canned preparation contains ascorbic acid in accordance with the present invention, whereas the comparative canned product containing no ascorbic acid shows substantially no reduction of oxygen.

Further the same samples were stored at 40°C for a predetermined period and the amount of the iron dissolved out from the can was measured to determine susceptibility to corrosion. The results are shown in Table 3 below.

Table 3

| | Amount in p.p.m. of iron dissolved | |
| Months | Example 1 | Comparative sample |
|---|---|---|
| 1 | 1.0 | 0.9 |
| 2 | 3.0 | 5.8 |
| 3 | 2.8 | 12.8 |
| 4 | 3.1 | 47.6 |
| 5 | 2.9 | 60.0 |
| 6 | 3.0 | 108.0 |

As evident from Table 3 above corrosion is effectively prevented with the canned product of the invention notwithstanding that it has a large head space (18 volume %), while with the comparative canned product containing no ascorbic acid corrosion increases with the lapse of storage period.

EXAMPLE 2

In 130 liters of water were dissolved 1.5 kg of sodium alginate and in the solution were suspended 300 kg of barium sulfate. In this suspension were dissolved 100 g of sodium erythorbate.

In a resin coated steel can, 250 ml in volume, were placed 133 ml of the resultant suspension and 67 ml of aerated water containing 3.0 gas volumes of carbon dioxide.

The air remained in the head space of the can was replaced with carbon dioxide in the same manner as described in Example 1.

The viscosity of this contrast medium was 220 c.p.s. and the comparative medium containing no sodium erythorbate was 490 c.p.s.

The air remaining in the resultant can with the lapse of time is shown in Table 4 below, in which are also shown the test results of the comparative sample prepared in the same manner as above without using sodium erythorbate.

Table 4

| Lapse of time | Sodium erythorbate added (mg%) | Air remained (ml) | Oxygen remained (ml) |
|---|---|---|---|
| 0 month | 0 | 5.5 | 1.1 |
|  | 50 | 5.7 | 1.0 |
| 1 week | 0 | 5.5 | 1.0 |
|  | 50 | 5.0 | 0.7 |
| 3 weeks | 0 | 5.4 | 1.1 |
|  | 50 | 4.4 | 0 |

The samples were stored at 40°C for predetermined period and the amount of iron dissolved out from the can was measured. The results are shown in Table 5 below.

Table 5

| | Amount in p.p.m. of iron dissolved | |
| Months | Example 2 | Comparative sample |
|---|---|---|
| 1 | 1.2 | 1.5 |
| 3 | 2.2 | 10.8 |
| 6 | 2.2 | 78.0 |

EXAMPLE 3

Four kinds of contrast media were prepared in accordance with the following formulation:

Sample A

| Barium sulfate | 75 g |
| Sodium alginate | 0.85 g |
| Carbon dioxide | 1.5 volume |
| Sodium ascorbate | 30 mg% |
| Water | Amount necessary for making 100 ml of suspension |

Sample B

The same as Sample A except that no sodium ascorbate was used

Sample C

| Barium sulfate | 120g |
| Sodium carboxymethyl cellulose | 0.8 g |
| Carbon dioxide | 0.75 volume |
| Erythorbic acid | 50 mg% |
| Water | Amount necessary for making 100 ml of suspension |

Sample D

The same as Sample C except that no erythorbic acid was used.

Viscosity of the samples thus obtained was as follows:

Table 6

| Samples | Viscosity (cps, at 25°C) |
|---|---|
| A | 180 |
| B | 385 |
| C | 370 |
| D | 1150 |

What we claim is:
1. An aqueous barium sulfate contrast medium which comprises barium sulfate, carbon dioxide, a suspending agent and an additive selected from the group consisting of ascorbic acid, erythorbic acid and a water-soluble alkali metal salt thereof, the barium sulfate concentration being at least 750 grams per liter of the medium, the carbon dioxide concentration being 0.2 to 4 gas volumes and the additive concentration being in the range of 1 mg% to 150 mg%.

2. The aqueous barium sulfate contrast medium according to claim 1, in which said water-soluble alkali metal salt is at least one of sodium ascorbate, potassium ascorbate, sodium erythorbate and potassium erythorbate.

3. The aqueous barium sulfate contrast medium according to claim 1, in which said additive concentration is in the range of 3 to 50 mg%.

* * * * *